United States Patent [19]

Shibasaki et al.

[11] Patent Number: 4,777,271

[45] Date of Patent: Oct. 11, 1988

[54] ISOCARBACYCLIN DERIVATIVES AND PROCESS FOR PRODUCTION THEREOF

[75] Inventors: Masakatsu Shibasaki, Mitaka; Mikiko Sodeoka; Toshiaki Mase, both of Sagamihara, Japan

[73] Assignee: Sagami Chemical Research Center, Tokyo, Japan

[21] Appl. No.: 65,218

[22] PCT Filed: Oct. 7, 1986

[86] PCT No.: PCT/JP86/00511

§ 371 Date: May 29, 1987

§ 102(e) Date: May 29, 1987

[87] PCT Pub. No.: WO87/02360

PCT Pub. Date: Apr. 23, 1987

[30] Foreign Application Priority Data

Oct. 14, 1985 [JP] Japan ................... 60-226972

[51] Int. Cl.$^4$ ........................... C07D 319/04
[52] U.S. Cl. ...................... 549/363; 549/214; 562/501
[58] Field of Search ................ 549/363, 214

[56] References Cited

U.S. PATENT DOCUMENTS 4,215,048  7/1980  Chen et al. ................ 549/363
4,530,925  7/1985  Collington et al. ......... 514/211

Primary Examiner—Nicky Chan
Attorney, Agent, or Firm—Wenderoth, Lind & Ponack

[57] ABSTRACT

An isocarbacyclin derivative represented by the general formula

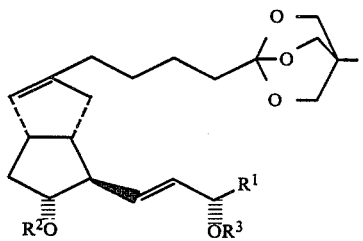

wherein $R^1$ represents a linear, branched or cyclic alkyl, alkenyl or alkynyl group having 5 to 10 carbon atoms, and $R^2$ and $R^3$ represent a hydrogen atom or a protective group for the hydroxyl group; and a process for production thereof.

1 Claim, No Drawings

ISOCARBACYCLIN DERIVATIVES AND PROCESS FOR PRODUCTION THEREOF

TECHNOLOGICAL FIELD

This invention relates to isocarbacyclin derivatives represented by the following general formula (I)

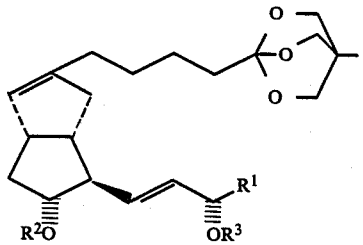

(I)

wherein $R^1$ represents a linear, branched or cyclic alkyl, alkenyl or alkynyl group having 5 to 10 carbon atoms, and $R^2$ and $R^3$ represent a hydrogen atom or a protective group for the hydroxyl group, and a process for production thereof.

The isocarbacyclin derivatives represented by general formula (I) provided by this invention can be converted to 9(O)-methano-$\Delta^{6(9\alpha)}$-$PGI_1$ (isocarbacyclin) and its analogs by hydrolyzing their ortho esters, and then when $R^2$ and $R^3$ are protective groups, removing the protective groups from the hydroxyl groups. Isocarbacyclin has strong platelet aggregation inhibiting activity. Its activity on, for example, human platelets is comparable to that of chemically unstable $PGI_2$, and it has been gaining acceptance as a therapeutic or prophylactic agent for various cardiovascular diseases (see Japanese Laid-Open Patent Publication No. 137445/1984).

BACKGROUND TECHNOLOGY

A method starting from furfural and goes through general formulae (II) and (III) has previously been known as the most efficient method of producing isocarbacyclin [Tetrahedron Letters, 25, 5087 (1984)].

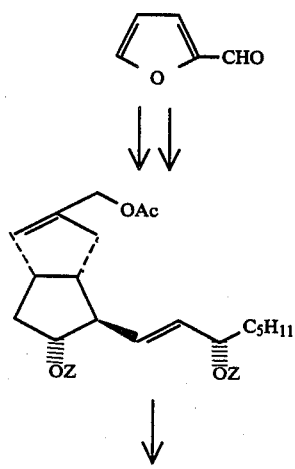

(II)

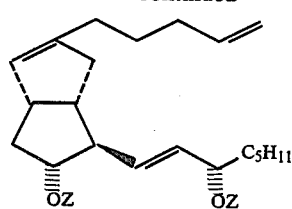

(III)

In the formulae, —OZ represents a t-butyldimethylsilyloxy group (same hereinafter).

According to this method, the step of deriving the triene compound of general formula (III) from the acetoxy compound of general formula (II) requires the use of 3-butenyllithium. Hence, it has the serious defect of using a very large amount of mercuric chloride for production of 3-butenyllithium. The present inventors studied a method of avoiding the use of mercury and further extensively worked in search of a method by which isocarbacyclin and its analogs can be synthesized in less process steps. These efforts have led to the discovery that isocarbacyclin and its analogs can be synthesized in less process steps by preparing the isocarbacyclin derivatives of general formula (I) and hydrolyzing them; and consequently, to the accomplishment of the present invention.

DETAILED DESCRIPTION OF THE INVENTION

The isocarbacyclin derivatives of general formula (I) in accordance with this invention can be produced by condensing bicyclo[3.3.0]octene derivatives represented by the general formula

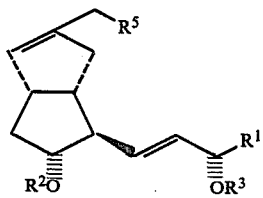

(IV)

wherein $R^1$ represents a linear, branched or cyclic alkyl, alkenyl or alkynyl group having 5 to 10 carbon atoms, $R^2$ and $R^3$ represent a hydrogen atom or a protective group for the hydroxyl group, and $R^5$ represents chloro, bromo, iodo, p-toluenesulfonyloxy or methanesulfonyloxy, with a lithium compound represented by the general formula

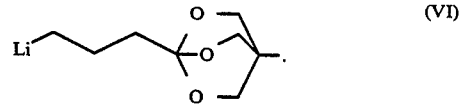

(VI)

The bicyclo[3.3.0]octene derivatives of general formula (IV) can be produced in accordance with the method described in the literature [Tetrahedron Letters, 25, 5087 (1984)].

$R^1$ in general formula (IV) represents a linear, branched or cyclic alkyl, alkenyl or alkynyl group having 5 to 10 carbon atoms. Examples include alkyl groups such as pentyl, hexyl, 1-methylpentyl, 2-methylpentyl, 2-methylhexyl, cyclopentyl and cyclohexyl; alkenyl groups such as 1-pentenyl, 2-pentenyl, 1-hexenyl, 2-hexenyl, 2-methyl-3-pentenyl, 1-methyl-4-pentenyl, 1,4-dimethyl-3-pentenyl, 6-methyl-5-heptenyl and 2,6-dimethyl-5-heptenyl; and alkynyl groups such as 2-pentynyl, 3-pentynyl, 1-methyl-2-pentynyl and 1-methyl-3-pentynyl.

$R^2$ and $R^3$ represent a hydrogen atom or a protective group for the hydroxyl group. Examples of the protective group for the hydroxyl group are tri($C_1$-$C_7$)-hydrocarbon-silyl groups such as trimethylsilyl, t-butyldimethylsilyl, t-butyldiphenylsilyl, dimethylphenyl and tribenzylsilyl; and groups forming an acetal linkage together with the oxygen atom of the hydroxyl group, such as methoxymethyl, 1-ethoxyethyl, (2-methoxyethoxy)methyl, benzyloxymethyl, 2-tetrahydrofuranyl, 2-tetrahydropyranyl and 6,6-dimethyl-3-oxa-2-oxobicyclo[3.1.0]hexa-4-yl.

The lithium compound of general formula (VI) is prepared from an ortho ester compound represented by the following general formula (V)

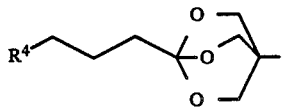

wherein $R^4$ represents bromo or iodo,
and, for example, a lithium naphthalene anion radical or t-butyllithium.

The ortho ester derivatives of general formula (V) can be easily synthesized by the method described in the literature [E. J. Corey et al., Tetrahedron Letters, 24, 5571 (1983)]. The lithium naphthalene anion radical can also be prepared by the method described in the literature [P. K. Freeman et al., J. Org. Chem., 45, 1924 (1980)].

Preparation of the lithium compound of formula (VI) from the ortho ester derivative of general formula (V) and the lithium naphthalene anion radical should be carried out in the presence of a solvent. Examples of the solvent are ether solvents such as tetrahydrofuran, diethyl ether and 1,2-dimethoxyethane. Use of tetrahydrofuran is preferred in order to carry out the reaction efficiently. The reaction usually proceeds smoothly at −78° C. to room temperature. In view of the reaction efficiency and the simplicity of the reaction operation, reaction temperatures around 0° C. are most suitable.

Preparation of the lithium compound of formula (VI) from the ortho ester derivative of general formula (V) and t-butyllithium can be carried out in accordance with the method described in the literature [E. J. Corey et al., Tetrahedron Letters, 24, 5571 (1983)]. The lithium compound of formula (VI) obtained by the above reaction is reacted with the bicyclo[3.3.0]octene derivative of general formula (IV). Tetrahydrofuran, diethyl ether, and 1,2-dimethoxyethane, for example, are the solvents that can be used in the reaction with the bicyclo[3.3.0]octene derivative, but to carry out the reaction efficiently, it is preferable to use tetrahydrofuran. The reaction usually proceeds smoothly at −100° C. to room temperature. To perform the reaction efficiently, reaction temperatures around −80° C. are most suitable.

As a result, the isocarbacyclin derivative of general formula (I) is obtained. The isocarbacyclin derivative can be converted to 9(O)-methano-$\Delta^{6(9\alpha)}$-$PGI_1$ (isocarbacyclin) and its analogs by hydrolyzing its ortho ester and when $R^2$ and $R^3$ are protective groups, subjecting the hydrolyzate to deprotecting reaction. Hydrolysis of the ortho ester is a method known per se, and, for example, involves treatment in an aqueous solution of lithium hydroxide, sodium hydroxide, potassium hydroxide or the like. The deprotecting reaction is also a method known per se. When the protective groups are tri($C_1$-$C_7$)-hydrocarbon-silyl groups, it is carried out by treating the protected compound with tetrabutyl ammonium fluoride, cesium fluoride, an aqueous solution of hydrogen fluoride, etc. When the protective groups are groups forming an acetal linkage together with the oxygen atom of the hydroxyl group, it can be carried out by treatment with acetic acid, a pyridium salt of p-toluenesulfonic acid, etc.

The following Referential Examples and Examples illustrate the present invention in greater detail.

EXAMPLE 1

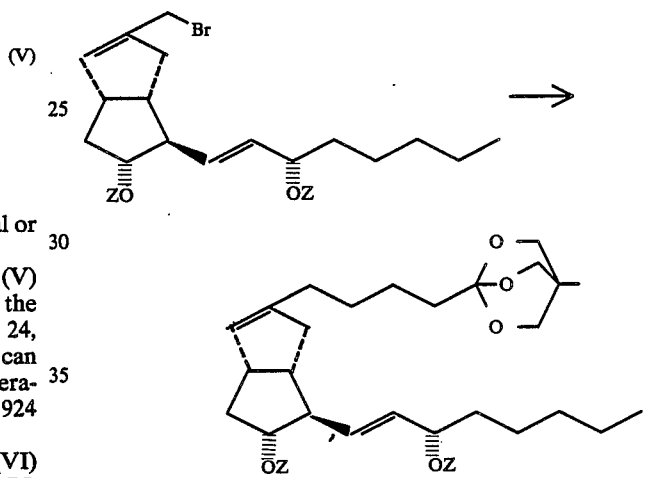

In an argon atmosphere, naphthalene (512 mg, 4 mmol) was dissolved in THF (15 ml), and small cut pieces of lithium (28 mg, 4 mmol) were added at room temperature. After ascertaining that coloration of the solution began, it was stirred under ice cooling for 5 hours. The resulting dark green solution was cooled to −80° C., and 1-(3-bromopropyl)-4-methyl-2,6,7-trioxabicyclo[2.2.1]octane (502 mg, 2 mmol) was added, and the mixture was stirred for 5 minutes. Furthermore, a THF solution (2 ml) of 3-bromomethyl-6-exo-[3-t-butyldimethylsilyloxy-1-(E)-octenyl]-7-endo-t-butyldimethylsilyloxybicyclo[3.3.0]oct-2-ene (75 mg, 0.13 mmol) was added at −80° C., and the mixture was stirred at −80° to −60° C. for 25 minutes. A saturated aqueous solution of ammonium chloride was added to the reaction mixture, and after elevating the temperature of the mixture to room temperature, it was extracted with diethyl ether. The ether layer was washed with saturated aqueous sodium chloride solution, and dried over anhydrous magnesium sulfate. The solvent was evaporated from the ether layer, and the residue was purified by silica gel column chromatography (50 g of silica gel treated with triethylamine; ether/n-hexane=1:20) to give 25 mg (29%) of the desired 3-[4-(4-methyl-2,6,7-trioxabicyclo[2.2.2]octyl)butyl]-6-exo-[3-t-butyldimethylsilyloxy-1-(E)-octenyl]-7-endo-t-butyldimethylsilyloxybicyclo[3.3.0]oct-2-ene as a nearly colorless oily substance.

NMR δ(CDCl₃): 5.42 (m, 2H), 5.18 (bs, 1H), 3.87 (s, 6H), 3.50–4.10 (m, 2H), 2.90 (m, 1H), 0.70–1.00 (m, 24H).

EXAMPLE 2

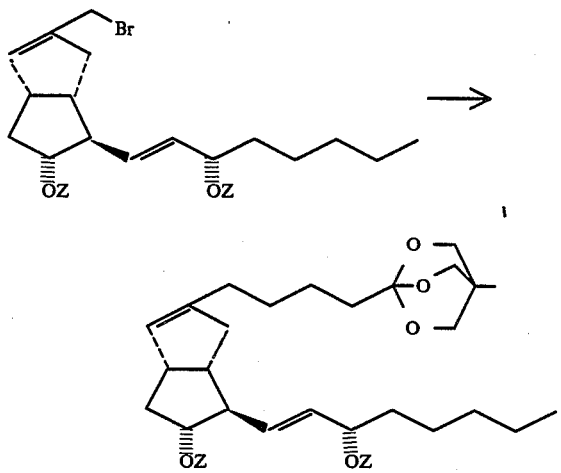

1-(3-Bromopropyl)-4-methyl-2,6,7-trioxabicyclo[2.2.-2]octane (36.6 mg, 0.146 mmol) was dissolved in tetrahydrofuran (0.5 ml), and a pentane solution of t-butyllithium (0.117 ml, 0.292 mmol) (2.5M pentane solution) was added at −80° C., and the mixture was stirred at this temperature for 15 minutes. A tetrahydrofuran (0.4 ml) solution of 3-bromomethyl-6-exo-[3-t-butyldimethylsilyloxy-1(E)-octenyl]-endo-t-butyldimethylsilyloxybicyclo[3.3.0]oct-2-ene was added dropwise at −80° C. The mixture was stirred at the above temperature for 30 minutes, then gradually heated, and stirred at 0° C. for 30 minutes. A saturated aqueous solution of ammonium chloride was added to the resulting reaction mixture, and the mixture was extracted wih diethyl ether. The ether layer was washed with a saturated aqueous solution of sodium chloride, and dried over anhydrous magnesium sulfate. The solvent was evaporated from the ether layer, and the residue was purified by silica gel column chromatography (50 g of triethylamine-treated silica gel; ether/n-hexane=1:20) to give the desired 3-[4-(4-methyl-2,6,7-trioxabicyclo[2.2.2]octyl)butyl]-6-exo-[3-t-butyldimethylsilyloxy-1-(E)-octenyl]-7-endo-t-butyldimethylsilyloxybicyclo[3.3.0]oct-2-ene (28 mg, 38%).

The NMR spectrum of the substance obtained by the foregoing reaction operations completely agreed with that of the product obtained in Example 1.

REFERENTIAL EXAMPLE 1

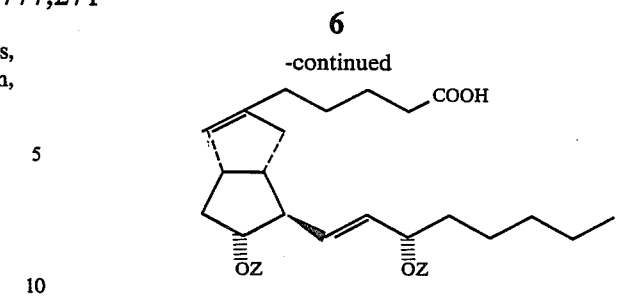

3-[4-(4-Methyl-2,6,7-trioxabicyclo[2.2.2]octyl)butyl]-6-exo-[3-t-butyldimethylsilyloxy-1-(E)-octenyl]-7-endo-7-butyldimethylsilyloxybicyclo[3.3.0]oct-2-ene (25 mg, 0.038 mmol) was dissolved in dimethoxyethane (0.1 ml), and an aqueous solution (0.1 ml) of sodium hydrogensulfate (6 mg, 0.042 mmol) was added to the solution at 0° C. The mixture was stirred at 0° C. for 30 minutes, and 2 ml of a 0.15M aqueous solution of lithium hydroxide was added. The mixture was stirred at room temperature for 8 hours. A 2N aqueous solution of hydrochloric acid was addd to the resulting reaction mixture to adjust its pH to 4 to 5, and the mixture was extracted with diethyl ether. The ether layer was dried over anhydrous sodium sulfate. The solvent was evaporated from the ether layer, and the residue was purified by silica gel column chromatography (ether/n-hexane=1:4) to give the desired bis-t-butylmethylsilyl ether (22 mg, 98%) of isocarbacyclin.

NMR δ(CDCl₃): 5.45 (m, 2H), 5.24 (m, 1H), 4.08 (m, 1H), 3.68 (m, 1H), 2.95 (m, 1H), 0.90 (s, 9H), 0.88 (s, 9H), 0.02 (s, 12H).

IR (neat): 2950 (br), 2850 (br), 1720, 1470, 1370, 1260 cm⁻¹.

Mass m/Z: 521 (M⁺-57).

REFERENTIAL EXAMPLE 2

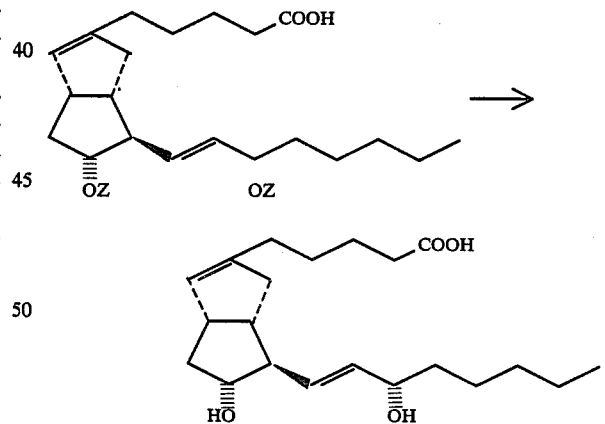

A tetrahydrofuran solution of tetrabutyl ammonium fluoride (0.1 ml, 0.1 mmol), 1M solution) was added to a tetrahydrofuran (0.3 ml) solution of the bis-t-butyldimethyl silyl ether (30 mg, 0.052 mmol) of isocarbacyclin, and the mixture was stirred at room temperature for 24 hours to perform reaction. Tetrahydrofuran was evaporated from the reaction mixture, and a saturated aqueous solution of sodium chloride was added. Diethyl ether was further added to extract the reaction mixture fully with it. The resulting ether layer was dried over anhydrous magnesium sulfate. The solvent was evaporated from the ether layer, and the residue was purified by short silica gel column chromatography (AcOET) to

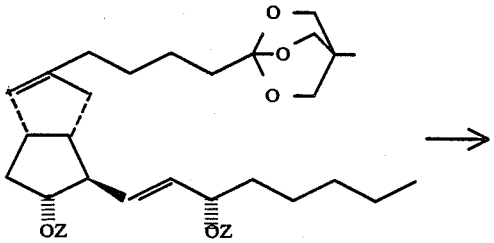

give the desired isocarbacyclin (15 mg, 83%). The spectral data of the isocarbacyclin obtained by the foregoing operations completely agreed with those described in the literature (Japanese Laid-Open Patent Publication No. 137445/1984).

We claim:

1. An isocarbacyclin derivative represented by the general formula

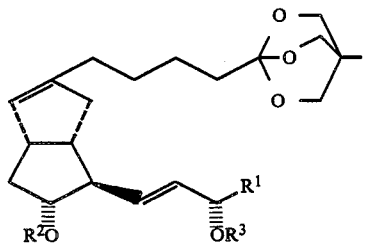

wherein $R^1$ represents a linear, branched or cyclic alkyl, alkenyl or alkynyl group having 5 to 10 carbon atoms, and
$R^2$ and $R^3$ represent a hydrogen atom or a protective group for the hydroxyl group.

* * * * *